(12) United States Patent
Krimmer et al.

(10) Patent No.: US 6,825,014 B2
(45) Date of Patent: Nov. 30, 2004

(54) PROCESS FOR THE PREPARATION OF ALLYSINE ACETAL

(75) Inventors: Hans-Peter Krimmer, Dietzenbach (DE); Oliver May, Frankfurt (DE); Ingo Klement, Pohlheim-Garbenteich (DE); Karlheinz Drauz, Freigericht (DE); Dietmar Reichert, Eschau (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/916,501

(22) Filed: Jul. 30, 2001

(65) Prior Publication Data

US 2002/0132848 A1 Sep. 19, 2002

(30) Foreign Application Priority Data

Jul. 28, 2000 (DE) .......................... 100 37 115

(51) Int. Cl.[7] .................... C12P 13/04; C12N 9/14; A61K 31/19
(52) U.S. Cl. .................... 435/106; 435/195; 514/477
(58) Field of Search ................. 435/106, 195; 514/477

(56) References Cited

FOREIGN PATENT DOCUMENTS

| EP | 0 625 571 | 11/1994 |
|----|-----------|---------|
| JP | 11-206397 | 8/1999 |
| WO | WO 00/58449 | 10/2000 |
| WO | WO 01/23535 | 4/2001 |
| WO | WO 01/23582 | 4/2001 |

OTHER PUBLICATIONS

Pietzsch, M., et al. (2000) J. Chromatog. B 737, 179–186.*
Syldatk, C., et al. (1988) Ann. N.Y. Acad. Sci. 542, 323–329.*

O. May, et al., Nature Biotechnology, vol. 18, No. 3, pp. 317–320, "Inverting Enantioselectivity by Directed Evolution of Hydantoinase for Improved Production of L–Methionine", Mar. 2000.

G. Wohlfahrt, et al., Dechema Biotechnology Conferences, vol. 5, No. Part A, pp. 45–48, "Immobilization of Hydantoin Cleaving Enzymes", 1992.

A. S. Bommarius, et al., Chirality, pp. 371–391, "Membrane Bioreactors for the Production of Enantiomerically Pure α–Amino Acids", 1992.

* cited by examiner

*Primary Examiner*—Charles L. Patterson, Jr.
(74) *Attorney, Agent, or Firm*—Oblon, Spivak, McClelland, Maier & Neustadt, P.C.

(57) ABSTRACT

The present invention relates to the preparation of compounds of formula (I):

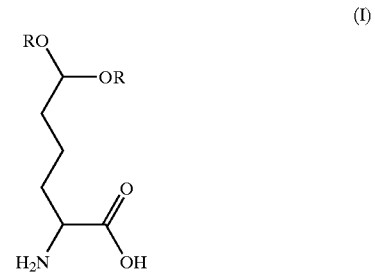

from the corresponding hydantoins by means of an enzymatic process. The L-compound is preferably formed.

18 Claims, No Drawings

PROCESS FOR THE PREPARATION OF ALLYSINE ACETAL

BACKGROUND OF THE INVENTION

1. Field of the Invention

The present invention is directed towards the preparation of compounds of the general formula (I):

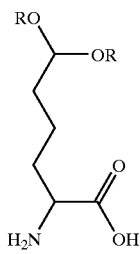
(I)

Such compounds are prepared in particular by means of an enzymatic process from hydantoins of the general formula (II):

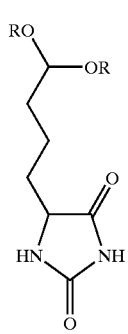
(II)

2. Description of Related Art

Compounds of formula (I) are suitable intermediates for the preparation of pharmaceuticals described in U.S. Pat. No. 5552397, WO 9738705 and in J. Med. Chem. 42, 305 (1999).

J. Med. Chem. 42, 305 (1999) mentions a synthesis route for the preparation of a structural unit—an α-amino-ε-caprolactam derivative—of the pharmaceutically active compounds. However, that structural unit is obtained with the aid of expensive reagents in a process that is rather disadvantageous for a robust commercial process.

The preparation of compounds such as (I) from hydantoins such as (II) by means of *Arthrobacter* sp. is already known from JP 99206397. However, that document does not describe the advantageous racemisation.

The conversion of hydantoins by means of hydantoinases and specific carbamoylases is already known from DE19529211.1. The spontaneous chemical racemisation of hydantoins for the preparation of enantiomerically enriched amino acids is to be found in DE-P4137581.5-44.

BRIEF DESCRIPTION OF THE INVENTION

Accordingly, one object of the present invention is to provide an enzymatic process for the preparation of the desired compounds of formulae (I), that is a simpler, more efficient, and less costly process suitable for large-scale commercial or industrial applications.

Another object of the invention is to provide a process for providing an allysine acetal in high yield and with a high degree of optical purity, for instance L-allysine acetal in a yield of about 85% or more, preferably at least 90% and most preferably >95%, and with an optical purity of at least 90%, preferably at least 95%, and most preferably >99% ee.

Yet another object of the invention is to provide a process that uses a total cell catalyst comprising a cell that has a gene encoding a hydantoin racemase, a hydantoinase and an L- or D-specific carbamoylase. For instance, a total cell catalyst comprising an L-specific carbamoylase.

Products and compositions comprising compounds of general formulae (I) and having a high degree of optical purity are advantageously used as intermediates for producing pharmacologically active products, or directly in pharmacological products.

Other objects of the invention are described or may be inferred from the following detailed description.

DETAILED DESCRIPTION OF THE INVENTION

The process according to the present invention comprises the preparation of an allysine acetal of the general formula (I):

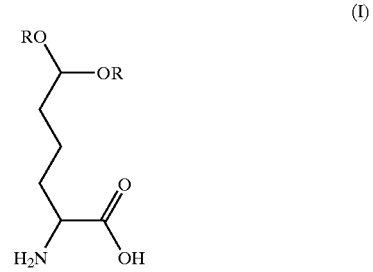
(I)

from a starting material comprising a hydantoin of the general formula (II):

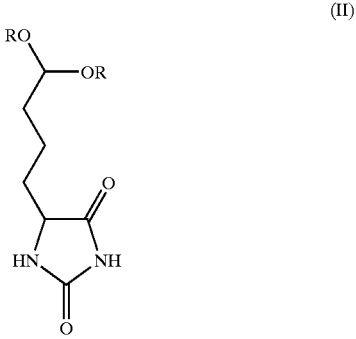
(II)

In both formulae (I) and (II) above: R represents ($C_1$–$C_8$)-alkyl, ($C_2$–$C_4$)-alkylenyl, preferably ethylenyl, ($C_6$–$C_{18}$)-aryl, ($C_7$–$C_{19}$)-aralkyl, or ($C_1$–$C_8$)-acyl.

($C_1$–$C_8$)-alkyl is a saturated hydrocarbon radical, such as methyl, ethyl, n-propyl, isopropyl, n-butyl, isobutyl, sec-butyl, tert-butyl, pentyl, hexyl, heptyl or octyl, including all their isomers.

A ($C_2$–$C_8$)-alkylenyl radical refers to an unsaturated hydrocarbon radical having from 2 to 8 carbon atoms containing at least one double bond, such as, for example, ethylenyl, propylenyl, etc. as well as isomers of these radicals.

A ($C_6$–$C_{18}$)-aryl radical is to be understood as being an aromatic radical having from 6 to 18 carbon atoms. It includes in particular groups such as phenyl, naphthyl, anthryl, phenanthryl, biphenyl radicals as well as isomers of these groups.

A ($C_7$–$C_{19}$)-aralkyl radical is a ($C_6$–$C_{18}$)-aryl radical bonded to the molecule via a ($C_1$–$C_8$)-alkyl radical.

A ($C_1$–$C_8$)-acyl radical denotes a ($C_1$–$C_8$)-alkyl radical that is bonded to the molecule via a C=O function.

The structures of the compounds shown in Formulas (I) and (II) above relate to both optical isomers.

Compounds of formula (II) are subjected to a reaction with at least one hydantoinase and at least one D- or L-specific carbamoylase, as well as to a spontaneous and/or enzyme-catalysed in situ racemisation. The enzymes involved may be used in free form, in immobilised form, as cell fractions or extracts or in a form enclosed in a cell. The desired compounds such as those of formula (I) are more easily obtained in advantageous yields and purities in a manner that is surprising for a large-scale process.

The reaction sequence according to the invention has hitherto not been applied in the prior art to the present compounds. It is therefore to be regarded as surprising that the labile acetal protecting group is stable under the reaction conditions and allysine acetal having an optical purity >99% ee can be generated in a very high yield from 100% of the hydantoin in an overall yield >85%.

As has been mentioned, the process according to the invention may be carried out partially enzymatically or completely enzymatically. In addition to the use of the free enzymes in a reaction batch, special preference is given, however, to a process in which there is used a so-called whole cell catalyst from a cell that has a cloned gene coding for a hydantoin racemase, a hydantoinase and an L- or D-specific carbamoylase. Such organisms are known in principle from U.S. Pat. No. 60/157427 (SEQ ID NO: 4/hydantoinase, SEQ ID NO:5/hydantoin racemase, SEQ ID NO:6/carbamoylase) or U.S. Pat No. 09/407062 (SEQ ID NO:1/hydantoinase, SEQ ID NO: 2/hydantoin racemase, SEQ ID NO: 3/carbamoylase). Accordingly, the disclosure of those specifications is regarded as being included herein, especially the disclosure of the relevant amino acid sequences in the sequence listings. That is the case especially for U.S. Pat. No. 60/157427.

The use of a total cell catalyst having an L-specific carbamoylase is most particularly advantageous. It is thus possible to obtain the desired optical antipode of allysine acetal for the preparation of pharmaceutically active substances.

In principle, the total cell catalyst may be any suitable expression system that comes into consideration for that purpose to those skilled in the art. Special preference is given, however, to the use of a recombinant bacterium, preferably E. coli, for this purpose. Advantageous E. coli strains include: JM109, NM 522, JM105, RR1, DH5α, TOP 10⁻ or HB101.

In order to carry out the invention, the following procedure is generally followed:
the substrate (II) is brought into contact with the enzymes in a suitable solvent, preferably water, at an optimum pH value for hydantoinase and carbamoylase of approximately from 5.5 to 8.5, preferably from 6.5 to 8, and at an optimum temperature for the enzyme activity of approximately from 20° C. to 40° C., preferably from 25° C. to 35° C.

Advantageously metal salts, such as $CoCl_2$ or $MgCl_2$, $MnCl_2$, etc., that have a positive effect on the enzyme activities may be added.

During cleavage of the hydantoins into the optically enriched amino acids, the hydantoins (or N-carbamoyl amino acids produced) racemise spontaneously. However, in order to accelerate that reaction, the hydantoin that remains can be racemised enzymatically in situ and is thus again available for cleavage into the amino acid. Enzymatic racemisation that proceeds simultaneously with the conversion of the hydantoin to the amino acid is preferred for reasons of simplicity, expediency or efficiency. All of the hydantoin can thus be converted into the amino acid in one step.

This reaction may be performed by using separate enzymes. Such enzymes may be in free or immobilised form, be contained within a cell fraction or extract or be enclosed inside of a microorganism (U.S. Ser. No. 60/157427).

The process according to the invention may be carried out in sequential reaction batches or continuously in a so-called enzyme-membrane reactor (Wandrey et al. in Jahrbuch 1998, Verfahrenstechnik und Chemieingenieurwesen, VDI p. 151 ff; Kragl et al. Angew. Chem. 1996, 6, 684 f).

Acetals produced by the processes of the present invention may be further purified by conventional methods known in the art, for instance, by separation of acetal from contaminants by centrifugation, extraction, or filtration and by recovering acetals by crystalization.

In a further embodiment, the invention relates to the use of the acetals prepared according to the invention as intermediates for synthesis or preparation of active ingredients, especially pharmaceutical compounds having biological activity.

Acetals prepared according to the processes of the present invention may also be directly incorporated into pharmaceutical compositions in combination with other pharmaceutically acceptable ingredients, excipients or carriers.

The following example further elaborates on one embodiment of the present invention. The process of the present invention may be practiced in other ways than as specifically described below and therefore is not limited by this example.

EXAMPLE 30 g (wet weight) of E. coli cells JM109 (pOM22, pOM21) (U.S. Ser. No. 60/157427) were mixed together with 100 mM DL-allysine hydantoin and 1mM $CoCl_2$ at pH 7.8 in 1 liter of water. The reaction mixture was then left for 4 hours at 37° C. The cells were then centrifuged off (45 min, 8000 rpm, 4° C., Beckman Coulter JA-10 rotor) and the supernatant was analysed by means of HPLC. After 4 hours, a yield of L-allysine acetal of >85% having an optical purity of >99% ee was obtained.

The modified hydantoinases that may be used in the present invention were produced, identified and isolated using random mutagenesis procedures of the type described in U.S. Pat. Nos. 5,316,935 and 5,906,930. Random mutagenesis protocols, which are also known as directed evolution procedures, are also described in Kuchner, O., Arnold, F. (1997) Directed Evolution of Enzyme Catalysts, TIBTECH 15:523–530; Chen, K. and Arnold F. (1991). Enzyme engineering for nonaqueous solvents—random mutagenesis to enhance activity of subtilisin E in polar organic media, Bio/Technology 9:1073–1077; Chen, K. and Arnold, F. (1993) Tuning the activity of an enzyme for unusual environments: sequential random mutagenesis of subtilisin E for catalysis in dimethylformamide, Proc. Natl. Acad. Sci. USA 90:56 18–5622; and You, L. and Arnold, F. H. (1996). Directed Evolution of Subtilisin E in Bacillus Subtilis to Enhance Total Activity in Aqueous Dimethylformamide, Protein Engineering, 9, 77–83.

The random mutagenesis procedure used to identify and isolate the modified hydantoinases followed the same basic procedures as identified above. First, a large number of random mutations in the wild type nucleotide sequence (SEQ. ID. NO. 7) were generated. This library of nucleotide sequences where then used to express a large number of mutated enzymes. The library of mutated hydantoinases was then screened to identify those mutants with enhanced enzymatic activity and changed enantioselectivity.

The step of screening the first library of expressed amino acid sequences to identify desirable variants could have been accomplished using any number of suitable screening techniques which measure desirable enzyme properties. The screening method actually used was a pH-indicator assay which will be described in more detail below.

In accordance with the present invention, four enzymes having enhanced hydantoinase properties were identified as the result of the first round of random mutagenesis of the DSM 9711 nucleotide sequence (SEQ. ID. NO. 7). The first round mutant enzymes are 1CG7, 11DH7, 1BF7 and 19AG 11. The nucleotide sequences for these first round mutants are set forth in SEQ. ID. NOS. 9, 11, 13 and 15, respectively. The corresponding amino acid sequences are set forth in SEQ. ID. NOS. 10, 12, 14 and 16, respectively.

A second round of random mutagenesis was conducted in which the 11 DH7 nucleotide sequence was randomly mutated to form a second library of mutants. A single mutant (22CG2) was identified which expressed a modified hydantoinase that exhibited desirable enzymatic properties. The 22CG2 enzyme is the same as the 11DH7 enzyme except that the 22CG2 mutant has an amino acid substitution at position 180.

The 22CG2 mutant was subjected to saturation mutagenesis in order to introduce all 20 different amino acids into amino acid position 95. 400 clones were screened and a mutant enzyme with enhanced enzymatic activity and higher (L)-selectivity was identified as Q2H4. The Q2H4 mutant is the same as the 22CG2 mutant except that phenylalanine is substituted for isoleucine at position 95.

As a result of the isolation and identification of the above identified mutants, it was established that improved hydantoinases may be obtained by modifying the DSM 9771 enzyme by substituting amino acids at positions 95, 124, 154, 180, 251 and 295. The substitutions may be made at one or more of the positions of SEQ. ID NO: 8. Table 1 sets forth preferred amino acid substitutions.

TABLE 1

| Amino Acid Position | Substitution | Abbreviation |
|---|---|---|
| 95 | Ile.fwdarw.Phe | I95F |
| 95 | Ile.fwdarw.Leu | I95L |
| 154 | Val.fwdarw.Ala | V154A |
| 180 | Val.fwdarw.Ala | V180A |
| 251 | Gln.fwdarw.Arg | Q251R |
| 295 | Val.fwdarw.Ala | IV295A |

Amino acid substitutions other than those set forth in Table 1 are possible provided that the resulting hydantoinase exhibits desirable enzymatic properties. For example, other suitable amino acid substitutions for isoleucine at position 95 include Gly, Ala, Val, Leu, Phe, Tyr and Trp. For positions 154, 180 and 295, suitable alternative amino acid substitutions for valine include Ala and Gly. Suitable alternative amino acid substitutions at position 251 for glutamine include Arg, Lys and Asn. The amino acid substitutions may be made by saturation mutagenesis followed by screening of clones. The substitutions may also be made by chemical manipulation of the DSM 9711 enzyme or by conventional synthesis of peptides having the desired amino acid substitutions at the desired locations. It should be noted that the above listed amino acid substitutions are intended to be exemplary of preferred alternative substitutions at the various substitution sites. Substitutions of other amino acids are possible provided that the enzymatic activity of the resulting protein is not destroyed. The usefulness of a particular amino acid substitution at positions 95, 154, 180, 251 and 295 can be determined by routine pH screening as described below. The amino acid substitutions described above may be made at equivalent positions in other hydantoinases. "Other hydantoinases" refers to enzymes that catalyze the hydrolysis of any 5'-mono- or disubstituted hydantoin derivative to yield the derived N-carbamoyl-amino acid and might have between 20 and 100% amino acid sequence identity to the hydantoinase from Arthrobacter sp. DSM 9771 which can be determined by sequence alignment algorithm such as BLAST (Altschul, S. F., Gish, W., Miller, W., Myers, E. W. & Lipman, D. J. (1990) "Basic local alignment search tool." J. Mol. Biol. 215:403–410).

Amino acid positions are numbered in a linear order (starting at the start codon) and not according to their functional and structural context. Therefore amino acid residues that contribute in the same way to an enzyme function of different hydantoinases do not necessarily have the same amino acid position number due to deletion or insertion events in the homologous enzyme. "Equivalent positions" of hydantoinases therefore refers to amino acid positions that contribute in the same way to a ftmction (activity or enantio-selectivity) as the amino acids identified in our evolution experiment. If the amino acid sequence identity of different hydantoinases is high, for example higher than 60%, and the amino acid position is located in a conserved region without sequence gaps, equivalent positions can be determined by sequence alignment using for example the BLAST algorithm. If the amino acid sequence identity is low, for example lower than 60%, and the amino acid position is located in a non-conserved region, or near gaps without being surrounded by regions of conserved amino acids, other methods such as structure alignments can be used if x-ray structures are available (Mizuguchi, K., Go, N., Seeking significance in 3-dimensional protein-structure comparisons. Cur. Opin. Struc. Biol. 5:377–382 (1995)). Here, backbone atoms are structurally aligned and equivalent positions can be found based on the relative locations of the amino acid residues of the structures.

An amino acid position that is identified for example by directed evolution to contribute to a specific function can often be occupied by different amino acid residues, not just the one that was identified by random point mutagenesis. Some substitutions will destroy the function, some of them will not change the function, and yet others will improve the function. With known methods, such as site saturation mutagenesis, one can easily identify amino acids that contribute in the same way to a function or even improve it by replacing the found amino acid residue with all possible amino acid residues (Miyazaki, K., Arnold, F., Exploring nonnatural evolutionary pathways by saturation mutagenesis: rapid improvement of protein function. J. Mol. Evol. 49:1716–1720). Even non-natural amino acids can be introduced at the identified site using a stop codon and a suppresser tRNA linked to a non-natural amino acid (Bain, J. D., Glabe, C. G., Dix, T. A., Chamberlain, A. R., Diala, E. S., Biosynthetic Site-Specific Incorporation Of A Non-Natural Amino-Acid Into A Polypeptide. JACS 111:8013–8014 (1989)).

Six modified hydantoinases in accordance with the present invention are listed in Table 2. Table 2 also lists the amino acid substitutions with respect to the DSM 9771 sequence (SEQ. ID. NO. 8) for each modified enzyme which is identified.

TABLE 2

| Hydantoinase Variant | Amino Acid Substitution |
| --- | --- |
| 1CG7 (SEQ. ID. NO. 10) | V154A |
| 11DH7 (SEQ. ID. NO. 12) | I95L + O251R |
| 1BF7 (SEQ. ID. NO. 14) | V295A |
| 19AG11 (SEQ. ID. NO. 16) | I95L |
| 22CG2 (SEQ. ID. NO. 18) | I95L + V180A + Q251R |
| Q2H4 (SEQ. ID. NO. 20) | I95F + V180A + Q251R |

The modified hydantoinases of the present invention may be used in the same manner as other hydantoinases to produce optically pure D- and L-amino acids. For example, see Biocatalytic Production of Amino Acids and Derivatives (Rozzell, J. D. and Wagner, F. eds.) (1992) Hanser Publisher, NY, at pages 75–176, for a description of the use of hydantoinases in the production of optically pure amino acids from DL-5-monosubstituted hydantoins. The general use of hydantoinases is also described in Enzyme catalysis in organic synthesis (Dranz, K. and Waldmann, H. eds.) 1995, VCH-Verlag, Weinheim, at pages 409–431; and Wagner, T. et al. (1996) Production of 1-methionine from d,1-5-(2-methylthioethyl) hydantoin by resting cells of a new mutant strain of Arthrobacter species DSM 7330, Journal of Biotechnology 46:63–68.

Amino acids referred to in the present invention are all natural or unnatural amino acids, wherein the amino acids are deemed to be a primary amine connected to carboxylic acid group via one intermediate C-atom (α-C-atom). This C-atom bears only one further residue. Preferred unnatural amino acids are disclosed in DE 19903268.8. Preferred natural amino acids are those mentioned in Beyer-Walter, Lehrbuch der Organischen Chemie, 22. Auflage, S. Hirzel Verlag Stuttgart, S.822–827. Among those amino acids presented above alanine, leucine, isoleucine, methionine, valine, tert-leucine or neopentyl glycine are not preferably transformed in a process utilizing the modified hydantoinase.

To transform hydantoins directly to the amino acids by enzymes it is preferred to use a whole-cell catalyst which includes the hydantoinase of the invention accompanied with a carbanioylase. A hydantoin racemase can also be used in addition to the hydantoinase and carbamoylase.

The hydantoinase can be used within this process either in their free or immobilized form. Also the carbamoylase and hydantoin racemase may be immobilized, too. Techniques to immobilize enzymes are well known to the skilled worker. Preferred methods are mentioned in Bhavender P. Shanna, Lorraine F. Bailey and Ralph A. Messing, Immobilisierte Biomaterialien-Techniken und Anwendungen, Angew. Chem. 1992, 94, 836–852; Dordick et al., J. Am. Chem. Soc. 194, 116, 5009–5010; Okahata et al., Tetrahedron Lett. 1997, 38, 1971–1974; Adlercreutz et al., Biocatalysis 1992, 6, 291–305; Goto et al., Biotechnol. Prog. 1994, 10, 263–268; Kamiya et al., Biotechnol. Prog. 1995, 11, 270–275; Okahata et al., Tibtech, February 1997, 15, 50–54; Fishman et al., Biotechnol. Lett. 1998, 20, 535–538).

The transformation discussed can be conducted in a batch process or continuous manner. Advantageously, an enzyme-membrane-reactor is used as the reaction vessel (Wandrey et al. in Jahrbuch 1998, Verfahrenstechnik und Chemieingenieurwesen, VDI S. 151ff.; Wandrey et al. in Applied Homogeneous Catalysis with Organometallic Compounds, Vol. 2, VCH 1996, S.832 ff; Kragl et al., Angew. Chem. 1996, 6, 684f.).

A further embodiment of the present invention is directed to a whole cell catalyst comprising a gene encoding for a carbamoylase, an optional racemase and a hydantoinase wherein the hydantoinase is considered to be according to the modified hydantoinase of the invention.

Advantageously, a bacteria is used as a cell, because of high reproduction rates and easy growing conditions to be applied. There are several bacteria known to the skilled worker which can be utilized in this respect. Preferably *E. coli* can be used as the cell and expression system in this regard (Yanisch-Perron et al., Gene (1985), 33, 103–109). Another aspect of the invention is a process for the production of enantiomerically enriched amino acids, which utilizes a whole cell catalyst according to the invention.

It is further preferred in this respect that amino acids like methionine, threonine, lysine or tert-leucine are produced by the aid of the whole cell catalyst.

The transformation discussed in this instance can be conducted in a batch process or continuous manner. Advantageously, an enzyme-membrane-reactor is used as the reaction vessel (Wandrey et al. in Jahibuch 1998, Verfabrenstechnik und Chemieingenieurwesen, VDI S. 151ff.; Wandrey et al. in Applied Homogeneous Catalysis with Organometallic Compounds, Vol. 2, VCH 1996, S832 ff.; Kragl et al., Angew. Chem. 1996, 6, 684f; DE 19910691.6).

There is a further aspect of the invention, which is directed to a process for the production of a whole cell catalyst of the invention. The process is preferably conducted by using expression vectors pOM17, pOM18, pOM20, pOM22 and/or pOM21. In addition primers of SEQ. NO. 23, SEQ. NO. 24, SEQ. NO. 21 and/or SEQ. NO. 22 are used with regard to the production of the whole cell catalyst.

Examples of Practice are as follows:

EXAMPLE 1

The following example provides additional details regarding the procedures used to identify and isolate the modified hydantoinases in accordance with the present invention.

The hydantoinase from *Arthrobacter* sp. DSM 9771 (U.S. Pat. No. 5,714,355) was cloned by polymerase chain reaction (PCR). The nucleotide sequence was determined and compared to other hydantoinases from closely related *Arthrobacter* strains. The nucleotide and amino acid sequences for the hydantoinase are set forth in SEQ. ID. NOS. 7 and 8, respectively. The cloned enzymes from *Arthrobacter* sp. DSM 9771 share about 97.5% identity based on their nucleotide sequence (corresponding to 7 amino acid changes) with the enzymes from *Arthrobacter aurescens* DSM 3747 and DSM 3745. The enzymes were expressed in *E. coli* JM109 using a rhamnose inducible vector construct which was provided by the Institute of Industrial Genetics, Universitait Stuttgart (Germany).

The hydantoinase was subjected to random mutagenesis using error-prone PCR. Approximately 10,000 clones were screened using a pH-indicator assay as described below:
1. Seed culture plates: plates containing 100 μl/well LBamp were inoculated with single colonies/well and incubated for 24 hours at 30° C., 250 rpm.
2. Main culture plates: cells from seed culture plates were transferred with a 96-pin replicator into plates containing 200 μl LBamp+0.2% rhamnose. Plates were incubated for 24 hours at 30° C., 250 rpm.

3. Assay: using a pipetting robot, the culture of each well was mixed by pipetting up and down (3×) and transferred (75 μl each) into two fresh plates. The two plates are filled with 100 μl/well freshly prepared substrate solution (80 mM D-MTEH and L-MTEH respectively, in 0.05 g/l cresol red pH 8.6). The absorbance at 580 nm is measured immediately after the substrate was added to the plate and after 3 hours incubation at room temperature. The activity was calculated as follows:

Activity=(A580(0 h)-A580(3 h))/((A580(0 h)-0.8))

(Rem:0.8 is the absorbance without cells)

For screening purposes, the ratio of activities for the D- and L-enantiomers is taken as an indicator for changed enantioselectivity.

Since the ratio of activities for different enantiomers in the screening tests is only a first hint of enantioselectivity, the identified mutants were confirmed by chiral HPLC using the racemic substrate as follows. 2 ml overnight cultures were added to 2 ml 80 mM DL-MTEH in 0.1M Tris pH8.5 and incubated at 37° C. After 1 h and 2 h respectively, the reaction mixture was centrifuged for 2 minutes, 14000 rpm. 20 μl of the supernatant was applied onto the HPLC column and the various fractions eluted.

About 2% of the population showed a significantly higher (>50%) activity compared to wild-type DSM 9771. Although a considerable number of those clones might be false positives due to common variation of expression level in a population, about 50% of rescreened clones were indeed higher activity mutants. The high number indicates that hydantoinase has a large evolutionary potential (its activity and enantioselectivity can be therefor improved). This can be rationalized since a high Km value (about 15 mM), a rather low specific activity (about 12 U/mg) and a low expression level (<10% of total protein) leaves room for improvements of this enzyme.

Table 3 shows the results of the tested mutants. Mutant 1CG7 shows a dramatic increase of (D-) selectivity. Compared to wild-type, the enantiomeric excess of the product is 4 times increased. The enantioselectivity of clone 11 DH7 and 19AG11 was changed into the opposite direction since both mutants are absolutely non-selective. The activity mutant 1BF7 possesses the same enantioselectivity as wild-type.

TABLE 3

| Clone | Conversion | enantiomeric excess [%] |
| --- | --- | --- |
| wild-type | 42% after 2 hours | 19 |
| 1CG7 | 42% after 2 hours | 90 |
| 11DH7 | 42% after 2 hours | 0 |
| 19AG11 | 37% after 2 hours | 0 |
| 1BF7 | 45% after 1 hour | 19 |

All of the mutants were sequenced and the nucleotide and amino acid sequences established as set forth in Table 4.

TABLE 4

|  | Nucleotide Sequence (SEQ. ID. NO.) | Amino Acid Sequence (SEQ. ID. NO.) |
| --- | --- | --- |
| 1CG7 | 9 | 10 |
| 11DH7 | 11 | 12 |
| 1BF7 | 13 | 14 |
| 19AG11 | 17 | 18 |

A second round of random mutagenesis was conducted using the first generation mutant 11 DH7 as the parent.

Two different libraries with different error rates (20% and 50% inactive clones) were produced and 10,000 clones of each library were screened using the above-described pH-indicator method. None of the screened clones showed significantly higher L-selectivity but mutants with improved activity and higher D-selectivity were found. One mutant (22CG2) differing in only one amino acid (V180A) from the parent was found to be 4-fold more active compared to parent 11DH7.

Sequencing of the first generation mutants 11DH7 and 19AGI 11 revealed a single mutation (I95L) is responsible for their decreased D-selectivity. Introducing all 20 different amino acids into amino acid position 95 of mutant 22CG2 by saturation mutagenesis and screening of about 400 clones revealed a new mutant (Q2H4) with significantly improved L-selectivity ($ee_L$=20%) and 1.5-fold improved activity compared to its parent 22CG2. The nucleotide and amino acid sequences for 22CG2 are set forth in SEQ. ID. NOS. 17 and 18, respectively. The nucleotide and amino acid sequences for Q2H4 are set forth in SEQ. ID. NOS. 19 and 20, respectively.

In addition to the improvements provided by the mutants described above, the activity of the whole cell catalyst could be increased by a factor of 10 by addition of 1 mM manganese to the growth medium and to the substrate solution. Under those conditions the activity of mutant 22CG2 was determined to be about 380 U/gCDW which is a 50-fold increase in activity compared to the activity described for *Arthrobacter* sp. DSM 9771.

All of the modified enzymes identified in accordance with the present invention have activities and/or enantioselectivity which are better than the unmodified DSM 9771 hydantoinase. When tested under standard conditions by HPLC, the Q2H4 mutant showed inverted enantioselectivity for the hydrolysis of D,L-MTEH. Q2H4 produced N-carbamoyl-L-methioine with an enantiomeric excess (ee) of 20% at about 30% conversion. In addition, the Q2H4 mutant was approximately 1.5-fold more active than its parent 22CG2.

EXAMPLE 2

In a further example, L-methionine was produced with a recombinant whole cell catalyst. Recombinant whole cell catalysts were prepared by co-expressing the evolved or wild-type hydantoinase with a hydantoin racemase and a L-carbamoylase in *E. coli* as follows.

Strains and expression vectors. The L-carbamoylase and hydantoinase expression vector pOM17 and pOM18 were constructed by PCR amplification of the hyuC and hyuH gene, respectively, from *Arthrobacter* sp. DSM 9771 using the following primer: for hyuC-amplification: 5'-AGGCGACATA-TGACCCTGCAGAAAGCGCAA-3' (SEQ. ID. NO. 23), 5'-ATGGOATCCCCGGT-CAAGTGCCTTCATTAC-3' (SEQ. ID. NO. 24); for hyuH-amplification: 5'-AGAACATATGTTTGACGT AATAGTTAAGAA-3' (SEQ. ID. NO.21), 5'-AAAAGGAT-CCTCACTTCGACGCCTCGTA-3' (SEQ. ID. NO. 22). The amplified fragments were cleaved with the restriction enzymes Ndel and BamHI and inserted using the same restriction enzymes downstream the rha BAD promoter (rhamnose promoter) into the vector pJOE2702 (Volif, J.-N., Eichenseer, C., Viell, P., Piendl, W. & Altenbuchner, J. (1996) Nucleotide sequence and role in DNA amplification of the direct repeats composing the amplificable element AUDI of Streptomyces lividans 66. Mol. Microbiol. 21, 1037–1047). The co-expression plasmid pOM20 comprising the L-carbamoylase and hydantoinase gene, both separately under the control of a rhamnose promoter, was derived from Plasmid pOM17 and pOM18. pOM17 was digested by SalI and treated with the Klenow fragment to form blunt ends. pOM18 was digested by BamII and also treated with the Klenow fragment to form blunt ends. Both fragments were subsequently digested from HindIu. The 1521 kb-fragment comprising the carbamoylase gene and rhamnose promoter derived from pOM17 was ligated with the 5650 kb-fragment of the digested pOM18 to yield pOM20. Mutations of the L-selective hydantoinase were introduced into pOM20 using the restriction enzymes RsrII and KasI which yielded pOM22. The racemase expression vector pOM21 was derived from pACYC184 (Rose, R. E. The nucleotide sequence of pACYC184. Nucleic Acids Res. 16, 355 (1988)) and carries a chloramphenicol selection marker and the racemase gene hyuR from *Arthrobacter* sp. D5M3747 under the control of the rhamnose promoter. All plasmids were routinely transformed into *E. coli* JM109 (Yanisch-Perron, C., Viera, J. & Messing, J. (1984) Improved M13 phage cloning vectors and host strains: nucleotide sequences of the M13 mp18 and pUC vectors. Gene 33, 103–109). The hydantoin converting pathway was installed in *E.coli* JM109 by transformation of pOM20 and pOM22, respectively into *E. coli* JM109 (pOM21). Cells were either grown in LB liquid medium or on LB-agar plates (Luria. S. E., Adams, J. N. & Ting, R. C. (1960) Transduction of lactose-utilizing ability among strains of *Escherichia coli* and *Shigella dysenteriac* and properties of phage particles. Virology 12, 348–390), both supplemented with the respective antibiotics for the growth and expression medium (100 μg/ml ampicillin, 50 μg/ml chioramphenicol) and addition of 2 mg/ml rhamnose for the expression medium.

Error-prone PCR. Random mutagenesis of the hydantoinase gene was performed in a 100 μl reaction mix containing 0.25 ng of plasmid DNA as template, Boebringer PCR buffer (10 mM Tris, 1.5 mM MgCl$_2$, 50 mM KCI, pH 8.3), 200 μM dATP, 200 μM dTTP, 200 μM dGTP, 200 μM dCTP, 50 pmol of each primer, and 2.5 U Taq polymerase (Boebringer). After 30 cycles, the 1667 amplification product was extracted from gel using the Qiaexll gel-extraction kit (Qiagen, Valencia, Calif.) and subdloned into vector pJOE2702 using the EcoRI and HindIII restriction sites. Religation frequency of alkaline phosphatase treated vector was below 1%.

Saturation mutagenesis. For randomization of the codon for amino acid position 95, the QuickChange.TM. protocol (Stratagene, La Jolla, Calif.) was used. About 10 ng plasmid from clone 22CG2 were amplified by PCR using two complimentary oligonucleotides (5'-CATCGAGATGCCGNNNACCTTCCCG-CCCAC-3', 5-GTGGGCGGGAAGGTNNNCGGCATCTCGATG-3'). After PCR amplification the reaction mixture was treated for 2 hours with 20 U of the restriction enzyme Dpnl. Transformation of 10 μl Dpnl digested reaction mixture into competent cells yielded a library of more than 2000 mutants of which about 400 were screened.

Preparation of library and screening. Single colonies of transformed *E. coli* were transferred into 384-well plates (master plates) using the robot system Qbot (Genetix, Dorset, UK). After 20 hour growth at 37° C. plates were stored at −80° C. For subsequent screening, plates were thawed and replicated into 96-well plates containing 200. mu.1 per well inductor medium. A Biomek 1000 pipetting workstation (Beckman, Fullerton, Calif.) was used to divide the 24 hours at 3° C. incubated plate into two fresh 96-well plates one containing 100 μl 80 mM L-MTEH the other 100 μl 80 mM D-MTEH in 50 mg/I cresol red solution adjusted to pH 8.5. Initial absorbance at 580 am and after 3 hours incubation at room temperature was measured using a THERMOmax plate reader (Molecular Devices, Sunnyvale, Calif.). Activity was calculated from the difference of initial and absorbance after 3 hours incubation divided by the cell density of each well. For the saturation mutagenesis library incubation time was reduced to 1.5 hours. The ratio of activity towards the L- and D-enantiomer was taken as a first indicator for enantioselectivity. Identified clones were then tested using the racemic substrate under conditions described below.

Characterization of activity and enantioselectivity. Plasmid of mutant found to be positive in the screen was sequenced and retransformed into *E. coli*. A culture of retransformed *E. coli* was grown for 16–18 hours (until OD10) in inductor medium supplemented with 1 mM MnCl$_2$. 2 ml substrate solution consisting of 80 mM D,L-MTEH, 0.1M Tris pH 8.5, 1 mM MnCl$_2$ (pre-incubated at 37° C.) were added to 2 ml cell culture (OD600-7). The reaction mixture was immediately incubated at 37° C. in a water bath. After different time periods (as specified in the text) 1 ml samples were taken and centrifuged for 5 minutes at 14,000 rpm. 20 μl of supernatant were analyzed by chiral HPLC using a column manufactured by Degussa-Huels AG. Activity was calculated from the amount of produced N-carbamoyl-D,L-methioine and expressed as U/mi cell culture of U/mg cell dry weight (CDW) were 1 U is the amount of whole-cell catalyst to produce 1 μmol N-carbamoyl-D,L-methionine in one minute under stated reaction conditions. Enantioselectivity of the hydantoinase and its mutants were compared by calculating the percentage of ee.sub.D ((D−L)/(D+L)) and ee$_L$ ((L−D)/(L+D)) respectively for the product at various extents of conversion. A conventional determination of E (enantiomeric ratio) from ee-values and the extent of conversion as described by Chen et al. (Chen, C. S., Fujimoto, Y., Girdaukas, G. & Sih, C. J. (1982) Quantitative analysis of biochemical kinetic resolutions of enantiomers. J Am. Chem. Soc. 104, 7294–7299) is not possible because of the fast racemization of the substrate.

Conversion of D,L-MTEH into L-met. 8 mg cell dry mass of *E. coli* JM109 (pOM20 & pOM21) and *E. coli* JM109 (pOM22 & pOM21) were added to 4 ml 100 mM D,L-MTEH in 0.1 M Tris pH 7.8 supplemented with 1 mM MnCl$_2$. The reaction mixture was incubated at 37° C. Samples were analyzed after indicated periods of time and analyzed by HPLC for MTEH, D,L-C met, and D,L-met as described in Volkel, D. & Wagner, F. Reaction (1995) mechanism for the conversion of 5-monosubstituted hydantoins to enantiomerically pure L-amino acids. Ann. NY Acad. Sci. 750, 1–9. The optical purity of the compounds was analyzed by chiral HPLC as described above.

The conversion of D,L-MTEH into L-met is significantly improved for the catalyst with the evolved hydantoinase. After three hours, approximately 60 mM L-met was produced from 100 mM D,L-MTEH, whereas the whole cell catalyst with the wild-type pathway produced only 10 mM of the amino acid. The concentration of the D-C met intermediate was reduced by a factor of 4 and the productivity for the production of L-amino acid was 8-fold increased during the first hour of the reaction.

EXAMPLE 3

The following example shows that production of L-methionine was significantly improved with an evolved hydantoinase of mutant 22CG2 which has improved activity and is not enantioselective (0% enantiomeric excess at 42% conversion, see Table 3). Mutations of the evolved hydantoinase from mutant 22CG2 were introduced into pOM20 as previously described using the restriction enzymes RsrII and KasI, which yielded pOM23. This co-expression vector was transformed into *E. coli* JM109 (pOM21). The resulting whole cell catalyst *E. coli* JM109 (pOM21/pOM23) and *E. coli* JM109 (pOM21/pOM20) were used for conversion of D,L-MTEH into methionine. 125 mg cell dry mass of the respective cells were added to 5 ml substrate solution (100 mM D,L-MTEH in 0.9% NaCl, 1 mM $MnCl_2$, pH 7.8) and incubated for 1 hour at 37° C. The whole cell catalyst with the improved hydantoinase from clone 22CG2 produced about 65 mM methionine within one hour whereas whole cell catalyst with the wild-type hydantoinase produced only 8 mM during the same reaction time. This demonstrates that an evolved hydantoinase without significant enantioselectivity but improved activity leads to a significant improvement for the production of methionine.

Modifications and Other Embodiments

Various modifications and variations of the described processes, products and compositions as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the biological, chemical, chemical engineering, medical or pharmacological arts or related fields are intended to be within the scope of the following claims.

Incorporation by Reference

Each document, patent application or patent publication cited by or referred to in this disclosure is incorporated by reference in its entirety. Any patent document to which this application claims priority is also incorporated by reference in its entirety. Specific incorporation by reference is made to DE 100 37 115.9, filed Jul. 28, 2000.

What is claimed is:

1. A process for the preparation of allysine acetal of the general formula (I)

comprising:

contacting a hydantoin of the general formula (II):

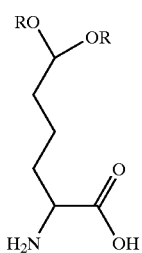

(I)

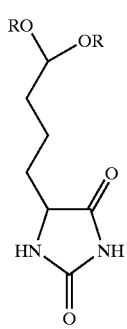

(II)

wherein in formulae (I) and (II) R represents $(C_1-C_8)$-alkyl, $(C_2-C_4)$-alkylene, $(C_6-C_{18})$-aryl, $(C_7-C_{19})$-aralkyl, or $(C_1-C_8)$-acyl, with a hydantoinase and a D- or L-specific carbamoylase in the presence of at least one hydantoin racemase, under conditions suitable for in situ racemisation of the hydantoin or of an N-carbamoyl amino acid.

2. The process of claim 1, wherein at least one of the hydantoinase, a D- or L-specific carbamoylase, or the at least one racemase is in at least one form selected from the group consisting of free form, immobilized form, cell fraction form, cell extract form, and in a form enclosed in a cell.

3. The process of claim 1, wherein the in situ racemization is spontaneous, enzyme-catalyzed, or both.

4. The process according to claim 1,
wherein the hydantoin racemase, the hydantoinase, and the L- or D- specific carbamoylase are present in a total cell catalyst.

5. The process according to claim 4,
wherein the total cell catalyst comprises an L-specific carbamoylase.

6. The process according to claim 4, wherein said total cell catalyst comprises L-specific carbamoylase.

7. The process according to claim 6, wherein the recombinant bacterium is *Escherichia coil*.

8. The process according to claim 1
wherein the contacting is carried out in an enzyme-membrane reactor.

9. The process according to claim 1, wherein the contacting is performed in the presence of a metal salt.

10. The process of claim 4, further comprising developing the total cell catalyst from at least one cell that comprises at least one cloned gene coding for at least one member selected from the group consisting of a hydantoin racemase, hydantoinase, L-specific carbamoylase, and D-specific carbamoylase.

11. The process of claim 4, wherein the total cell catalyst is at least one member selected from the group consisting of *Escherichia coil* JM109, *Escherichia coli* NM 522, *Escherichia coli* JM105, *Escherichia coli* RR1, *Escherichia coli* DH5, *Escherichia coli* TOP 10, and *Escherichia coli* HB101.

12. A method for producing a pharmaceutical or a biologically active product, comprising contacting the allysine acetal of the general formula (I) produced by the process of claim 1 with a pharmaceutically-acceptable or a biologically-acceptable ingredient, excipient, or carrier.

13. The process of claim 1, wherein the contacting is performed so that the allysine acetal of the general formula (I) is produced at an optical purity of at least 90%.

14. The process of claim 1, wherein the contacting is performed so that the allysine acetal of the general formula (I) is produced at a yield of at least 85%.

15. The process according to claim 1, wherein the contacting is performed at a pH of from 5.5 to 8.5.

16. The process according to claim 1, wherein the contacting is performed at a temperature of from 20 to 40° C.

17. A process for the preparation of allysine acetal of the general formula (I)

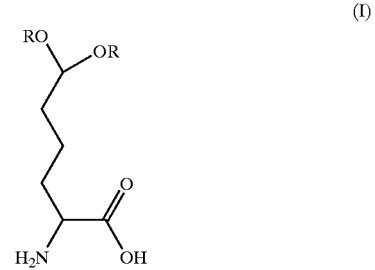

(I)

comprising:

contacting a hydantoin of the general formula (II):

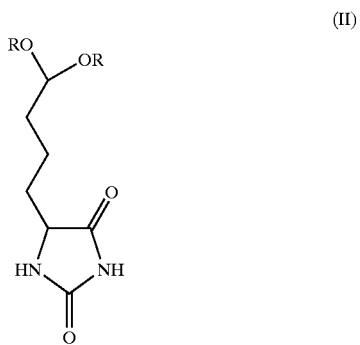

(II)

wherein in formulae (I) and (II) R represents $(C_1-C_8)$-alkyl, $(C_2-C_4)$-alkylene, $(C_6-C_{18})$-aryl, $(C_7-C_{19})$-aralkyl, or $(C_1-C_8)$-acyl, with a hydantoinase;

contacting the hydantoin with a D- or L-specific carbamoylase; and contacting the hydantoin with at least one hydantoin racemase, wherein the contacting is performed under conditions suitable for in situ racemisation of the hydantoin or of an N-carbamoyl amino acid.

18. The process according to claim 17, wherein the contacting of the hydantoin with the hydantoinase, D- or L-specific carbamoylase, and the at least one racemase are performed sequentially or continuously.

* * * * *

SEQUENCE LISTING

<160> NUMBER OF SEQ ID NOS: 24

<210> SEQ ID NO 1
<211> LENGTH: 1377
<212> TYPE: DNA
<213> ORGANISM: Arthrobacter aurescens

<400> SEQUENCE: 1

| | | | | | |
|---|---|---|---|---|---|
| atgtttgacg | taatagttaa | gaactgccgt | atggtgtcca | gcgacggaat | caccgaggca | 60 |
| gacattctgg | tgaaagacgg | caaagtcgcc | gcaatcagcg | cggacacacg | tgatgtcgag | 120 |
| gccagccgaa | ccattgacgc | gggtggcaag | ttcgtgatgc | cgggcgtggt | cgatgaacat | 180 |
| gtgcatatca | tcgacatgga | tctcaagaac | cggtatggcc | gcttcgaact | cgattccgag | 240 |
| tctgcggccg | tgggaggcat | caccaccatc | atcgagatgc | cgatcacctt | cccacccacc | 300 |
| accactctgg | acgccttcct | tgaaaagaag | aagcaggcgg | ggcagcggtt | gaaagttgac | 360 |
| ttcgcgctct | atggaggtgg | agtgccggga | aacctgcccg | agatccgcaa | aatgcacgac | 420 |
| gccggcgctg | tgggcttcaa | gtcaatgatg | gcagcctcag | tgccgggcat | gttcgacgcc | 480 |
| gtcagcgacg | gcgaactgtt | cgaaatcttc | caagagatcg | cagcctgtgg | ttcagtcatc | 540 |
| gtggttcatg | ccgagaatga | aacgatcatt | caagcgctcc | agaagcagat | caaggccgct | 600 |
| ggcggcaagg | acatggccgc | ctacgaggca | tcccaaccag | ttttccagga | gaacgaggcc | 660 |
| attcagcgtg | cgttgcttct | gcagaaagaa | gccggctgtc | gactgatcgt | gcttcacgtg | 720 |
| agcaaccctg | acggcgtcga | gttaatacat | caggcgcaat | ccgagggtca | ggacgtccac | 780 |
| tgcgagtcgg | gtccgcagta | tctgaatatc | accacggacg | acgccgaacg | aatcggaccg | 840 |
| tatatgaagg | tcgcgccgcc | cgtccgctca | gccgaaatga | acgtcaggtt | atgggaacaa | 900 |
| ctcgagaacg | gtgtcatcga | cacccttgga | tcagatcatg | gcggacatcc | tgtcgaggac | 960 |
| aaagaacccg | gctggaagga | cgtgtggaaa | gccggcaacg | gtgcgctggg | ccttgagaca | 1020 |
| tccctgccta | tgatgctgac | caacggagtg | aacaagggca | ggctatcctt | ggaacgcctc | 1080 |
| gtcgaggtga | tgtgcgagaa | acctgcgaag | cttttttggta | tctatccgca | gaagggcacg | 1140 |
| ctacaggttg | gttccgacgc | cgatctactc | atcctcgatc | tggacattga | caccaaagtg | 1200 |
| gatgcgtcgc | agttccgatc | cctgcataag | tacagcccgt | tcgacgggat | gcccgtcacg | 1260 |
| ggtgcaccgg | ttctgacgat | ggtgcgcgga | acggtggtgg | ccgagcaggg | agaagttctg | 1320 |

-continued gtcgagcagg gattcggcca gttcgtcacc cgtcaccact acgaggcgtc gaagtga    1377

<210> SEQ ID NO 2
<211> LENGTH: 711
<212> TYPE: DNA
<213> ORGANISM: Arthrobacter aurescens

<400> SEQUENCE: 2
atgagaatcc tcgtgatcaa ccccaacagt tccagcgccc ttactgaatc ggttgcggac     60
gcagcacaac aagttgtcgc gaccggcacc ataatttctg ccatcaaccc ctccagagga    120
cccgccgtca ttgaaggcag cttt gacgaa gcactggcca cgttccatct cattgaagag    180
gtggagcgcg ctgagcggga aaacccgccc gacgcctacg tcatcgcatg tttcggggat    240
ccgggacttg acgcggtcaa ggagctgact gacaggccag tggtaggagt tgccgaagct    300
gcaatccaca tgtcttcatt cgtcgcggcc accttctcca ttgtcagcat cctcccgagg    360
gtcaggaaac atctgcacga actggtacgc aagcggggg cgacgaatcg cctcgcctcc    420
atcaagctcc caaatctggg ggtgatggcc ttccatgagg acgaacatgc cgcactggag    480
acgctcaaac aagccgccaa ggaggcggtc caggaggacg cgccgagtc gatagtgctc    540
ggatgcgccg gcatggtggg gttt gcgcgt caactgagcg acgaactcgg cgtccctgtc    600
atcgacccg tcgaggcagc ttgccgcgtg gccgagagtt tggtcgctct gggctaccag    660
accagcaaag cgaactcgta tcaaaaaccg acagagaagc agtacctcta g          711

<210> SEQ ID NO 3
<211> LENGTH: 1239
<212> TYPE: DNA
<213> ORGANISM: Arthrobacter aurescens

<400> SEQUENCE: 3
atgaccctgc agaaagcgca agcggcgcgc attgagaaag agatccggga gctctcccgg     60
ttctcggcag aaggccccgg tgttacccgg ctgacctaca ctccagagca tgccgccgcg    120
cgggaaacgc tcattgcggc tatgaaagcg gccgccttga gcgttcgtga agacgcactc    180
ggaaacatca tcggccgacg tgaaggcact gatccggagc ttcctgcgat cgcggtcggt    240
tcacacttcg attctgtccg aaacggcggg atgtttgatg gcactgcagg cgtggtgtgc    300
gcccttgagg ctgcccgggt gatgctggag aacggctacg tgaatcggca tccatttgag    360
ttcatcgcga tcgtggagga ggaaggggcc cgcttcagca gtggcatgtt gggcggccgg    420
gccattgcag ggttggtcgc cgacagggaa ctggactctt tggttgatga ggatggagtg    480
tccgttaggc aggcggctac tgccttcggc ttgaagccgg gcgaactgca ggctgcagcc    540
cgctccgcgg cggacctgcg tgcttttatc gaactacaca ttgaacaagg accgatcctc    600
gagcaggagc aaatagagat cggagttgta acctccatcg ttggcgttcg cgcattgcgg    660
gttgccgtca aggcagaag cgaccacgcc ggcacaaccc ccatgcacct gcgccaggat    720
gcgctggtac cgccgctct catggtgagg gaggtcaacc ggttcgtcaa cgagatcgcc    780
gatgcacag tggctaccgt tggccacctc acagtggccc ccgtggagg caaccaggtc    840
ccgggggagg tggacttcac actggacctg cgttctccgc atgaggagtc gctccgcgtg    900
ctgatcgacc gcatctcggt catggtcggc gaggtcgcct cccaggccgg tgtggctgcc    960
gatgtggatg aatttttcaa tctcagcccg gtgcagctgg ctcctaccat ggtggacgcc   1020
gttcgcgaag cggcctcggc cttgcagttc acacaccggg atatcagcag tggggcgggc   1080
cacgactcga tgttcatcgc ccaggtcacg gacgtcggaa tggttttcgt tccaagccgt   1140

```
gctggccgga gccacgttcc cgaagaatgg accgatttcg atgaccttcg caaaggaact    1200
gaggttgtcc tccgggtaat gaaggcactt gaccggtaa                           1239

<210> SEQ ID NO 4
<211> LENGTH: 1377
<212> TYPE: DNA
<213> ORGANISM: Artificial Sequence
<220> FEATURE:
<223> OTHER INFORMATION: Synthetic DNA

<400> SEQUENCE: 4
atgtttgacg taatagttaa gaactgccgt atggtgtcca gcgacggaat caccgaggca      60
gacattctgg tgaaagacgg caaagtcgcc gcaatcagct cggacacaag tgatgttgag     120
gcgagccgaa ccattgacgc gggtggcaag ttcgtgatgc cgggcgtggt cgatgaacat     180
gtgcatatca tcgacatgga tctgaagaac cggtatggcc gcttcgaact cgattccgag     240
tctgcggccg tgggaggcat caccaccatc tttgagatgc cgtttacctt cccgcccacc     300
accactttgg acgccttcct cgaaaagaag aagcaggcgg ggcagcggtt gaaagttgac     360
ttcgcgctct atggcggtgg agtgccggga aacctgcccg agatccgcaa aatgcacgac     420
gccggcgcag tgggcttcaa gtcaatgatg gcagcctcag ttccgggcat gttcgacgcc     480
gtcagcgacg gcgaactgtt cgaaatcttc caggagatcg cagcctgtgg ttcagtcgcc     540
gtggtccatg ccgagaatga acgatcatt  caagcgctcc agaagcagat caaagccgct     600
ggtcgcaagg acatggccgc ctacgaggca tcccaaccag ttttcaggga gaacgaggcc     660
attcagcgtg cgttactact gcagaaagaa gccggctgtc gactgattgt gcttcacgtg     720
agcaaccctg acggggtcga gctgatacat cgggcgcaat ccgagggcca ggacgtccac     780
tgcgagtcgg gtccgcagta tctgaatatc accacggacg acgccgaacg aatcggaccg     840
tatatgaagg tcgcgccgcc cgtccgctca gccgagatga acgtcagatt atgggaacaa     900
cttgagaacg ggctcatcga caccctgggg tcagaccacg cggacatcc  tgtcgaggac     960 aaagaacccg gctggaagga cgtgtggaaa gccggcaacg tgcgctggg  ccttgagaca    1020 tccctgccta tgatgctgac caacggagtg aataaaggca ggctatcctt ggaacgcctc    1080
gtcgaggtga tgtgcgagaa acctgcgaag ctctttggca tctatccgca gaagggcacg    1140
ctacaggttg gttccgacgc cgatctgctc atcctcgatc tggatattga caccaaagtg    1200
gatgcctcgc agttccgatc cctgcataag tacagcccgt tcgacgggat gcccgtcacg    1260
ggtgcaccgg ttctgacgat ggtgcgcgga acggtggtgg cagagaaggg agaagttctg    1320
gtcgagcagg gattcggcca gttcgtcacc cgtcacgact acgaggcgtc gaagtga       1377

<210> SEQ ID NO 5
<211> LENGTH: 711
<212> TYPE: DNA
<213> ORGANISM: Arthrobacter aurescens

<400> SEQUENCE: 5
atgagaatcc tcgtgatcaa ccccaacagt tccagcgccc ttactgaatc ggttgcggac      60
gcagcacaac aagttgtcgc gaccggcacc ataatttctg ccatcaaccc ctccagagga     120
cccgccgtca ttgaaggcag cttttgacgaa gcactggcca cgttccatct cattgaagag    180
gtggagcgcg ctgagcggga aaacccgccc gacgcctacg tcatcgcatg tttcggggat     240
ccgggacttg acgcggtcaa ggagctgact gacaggccag tggtaggagt tgccgaagct     300
```

-continued

```
gcaatccaca tgtcttcatt cgtcgcggcc accttctcca ttgtcagcat cctcccgagg      360
gtcaggaaac atctgcacga actggtacgg caagcggggg cgacgaatcg cctcgcctcc      420
atcaagctcc caaatctggg ggtgatggcc ttccatgagg acgaacatgc cgcactggag      480
acgctcaaac aagccgccaa ggaggcggtc caggaggacg cgccgagtc gatagtgctc       540 ggatgcgccg gcatggtggg gtttgcgcgt caactgagcg acgaactcgg cgtccctgtc      600
atcgaccccg tcgaggcagc ttgccgcgtg gccgagagtt tggtcgctct gggctaccag      660
accagcaaag cgaactcgta tcaaaaaccg acagagaagc agtacctcta g               711
```

<210> SEQ ID NO 6
<211> LENGTH: 1263
<212> TYPE: DNA
<213> ORGANISM: Arthrobacter aurescens
<220> FEATURE:
<221> NAME/KEY: misc_feature
<222> LOCATION: (25)..(25)
<223> OTHER INFORMATION: n = any nucleotide

<400> SEQUENCE: 6

```
atgaccctgc agaaagcgca agcgnagcgc attgagaaag agatctggga gctctcccgg       60
ttctcggcgg aaggccccgg tgttacccgg ctgacctaca ctccagagca tgccgccgcg      120
cgggaaacgc tcattgcggc tatggaagcg ccgctttga gcgttcgtga agacgctctc       180
gggaacatca tcggccgacg tgaaggcact gatccgcagc tccctgcgat cgcggtcggt      240
tcacacttcg attctgtccg aaacggcggg atgttcgatg gcactgcagg cgtggtgtgc      300
gcccttgagg ctgcccgggt gatgctggag agcggctacg tgaatcggca tccatttgag      360
ttcatcgcga tcgtggagga ggaaggggcc cgcttcagca gtggcatgtt gggcggccgg      420
gccattgcag gtttggtcgc cgacagggaa ctggactctt tggttgatga ggatggagtg      480
tccgttaggc aggcggctac tgccttcggc ttgaagccgg gcgaactgca ggctgcagcc      540
cgctccgcgg cggacctgcg tgcttttatc gaactacaca ttgaacaagg accgatcctc      600
gagcaggagc aaatagagat cggagttgtg acctccatcg ttggcgttcg cgcattgcgg      660
gttgctgtca aaggcagaag cgcacacgcc ggcacaaccc ccatgcacct gcgccaggat      720
gcgctggtac ccgccgctct catggtgcgg gaggtcaacc ggttcgtcaa cgagatcgcc      780
gatggcacag tggctaccgt tggccacctc acagtggccc ccggtggcgg caaccaggtc      840
ccgggggagg tggagttcac actggacctg cgttctccgc atgaggagtc gctccgggtg      900
ttgatcaacc gcatctcggt catggtcggc gaggtcgcct cgcaggccgg tgtggctgcc      960
gatgtggatg aattttttcaa tctcagcccg gtgcagctgg ctcctaccat ggtggacgcc     1020
gttcgcgaag cggcctcggc cctgcagttc acgcaccggg atatcagcag tggggcgggc     1080
cacgactcga tgttcatcgc ccaggtcacg gacgtcggaa tggttttcgt tccaagccgt     1140
gctgccggga gccacgttcc cgaagaatgg accgatttcg atgaccttcg caagggaact     1200
gaggttgtcc tccgggtaat gaaggcactt gaccggggat cccatcatca tcatcatcat     1260
tga                                                                   1263
```

<210> SEQ ID NO 7
<211> LENGTH: 1377
<212> TYPE: DNA
<213> ORGANISM: Arthrobacter sp.

<400> SEQUENCE: 7

```
atgtttgacg taatagttaa gaactgccgt atggtgtcca gcgacggaat caccgaggca       60
```

| | |
|---|---|
| gacattctgg tgaaagacgg caaagtcgcc gcaatcagct cggacacaag tgatgttgag | 120 |
| gcgagccgaa ccattgacgc gggtggcaag ttcgtgatgc cgggcgtggt cgatgaacat | 180 |
| gcgagccgaa ccattgacgc gggtggcaag ttcgtgatgc cgggcgtggt cgatgaacat | 240 |
| tctgcggccg tgggaggcat caccaccatc atcgagatgc cgataacctt cccgcccacc | 300 |
| accactttgg acgccttcct cgaaaagaag aagcaggcgg gcagcggtt gaaagttgac | 360 |
| ttcgcgctct atggcggtgg agtgccggga aacctgcccg agatccgcaa aatgcacgac | 420 |
| gccggcgcag tgggcttcaa gtcaatgatg gcagcctcag ttccgggcat gttcgacgcc | 480 |
| gtcagcgacg gcgaactgtt cgaaatcttc caggagatcg cagcctgtgg ttcagtcgtc | 540 |
| gtggtccatg ccgagaatga aacgatcatt caagcgctcc agaagcagat caaagccgct | 600 |
| ggtcgcaagg acatggccgc ctacgaggca tcccaaccag tttccagga gaacgaggcc | 660 |
| attcagcgtg cgttactact gcagaaagaa gccggctgtc gactgattgt gcttcacgtg | 720 |
| agcaaccctg acggggtcga gctgatacat caggcgcaat ccgagggcca ggacgtccac | 780 |
| tgcgagtcgg gtccgcagta tctgaatatc accacggacg acgccgaacg aatcggaccg | 840 |
| tatatgaagg tcgcgccgcc cgtccgctca gccgagatga acgtcagatt atgggaacaa | 900 |
| cttgagaacg ggctcatcga caccttgggt caggaccacg gcggacatcc tgtcgaggac | 960 |
| aaagaacccg gctggaagga cgtgtggaaa gccggcaacg gtgcgctggg ccttgagaca | 1020 |
| tccctgccta tgatgctgac caacggagtg aataaaggca ggctatcctt ggaacgcctc | 1080 |
| gtcgaggtga tgtgcgagaa acctgcgaag ctctttggca tctatccgca gaagggcacg | 1140 |
| ctacaggttg gttccgacgc cgatctgctc atcctcgatc tggatattga caccaaagtg | 1200 |
| gatgcctcgc agttccgatc cctgcataag tacagcccgt cgacgggat gcccgtcacg | 1260 |
| ggtgcaccgg ttctgacgat ggtgcgcgga acggtggtgg cagagaaggg agaagttctg | 1320 |
| gtcgagcagg gattcggcca gttcgtcacc cgtcacgact acgaggcgtc gaagtga | 1377 |

<210> SEQ ID NO 8
<211> LENGTH: 458
<212> TYPE: PRT
<213> ORGANISM: Arthrobacter sp.

<400> SEQUENCE: 8

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Phe Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

```
Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
                195                 200                 205

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
                275                 280                 285

Arg Ser Ala Glu Met Asn Val Arg Leu Trp Glu Gln Leu Glu Asn Gly
        290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
            355                 360                 365

Ala Lys Leu Phe Glu Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
450                 455

<210> SEQ ID NO 9
<211> LENGTH: 1377
<212> TYPE: DNA
<213> ORGANISM: Arthrobacter sp.

<400> SEQUENCE: 9
atgtttgacg taatagttaa gaactgccgt atggtgtcca gcgacggaat caccgaggca    60
gacattctgg tgaaagacgg caaagtcgcc gcaatcagct cggacacaag tgatgttgag   120
gcgagccgaa ccattgacgc gggtggcaag ttcgtgatgc cgggcgtggt cgatgaacat   180
gcgagccgaa ccattgacgc gggtggcaag ttcgtgatgc cgggcgtggt cgatgaacat   240
tctgcggccg tgggaggcat caccaccatc atcgagatgc cgataacctt cccgcccacc   300
```

-continued

```
accactttgg acgccttcct cgaaaagaag aagcaggcgg ggcagcggtt gaaagttgac     360
ttcgcgctct atggcggtgg agtgccggga aacctgcccg agatccgcaa aatgcacgac     420
gccggcgcag tgggcttcaa gtcaatgatg gcagcctcag ctccgggcat gttcgacgcc     480
gtcagcgacg gcgaactgtt cgaaatcttc caggagatcg cagcctgtgg ttcagtcgtc     540
gtggtccatg ccgagaatga aacgatcatt caagcgctcc agaagcagat caaagccgct     600
ggtcgcaagg acatggccgc ctacgaggca tcccaaccag ttttccagga gaacgaggcc     660
attcagcgtg cgttactact gcagaaagaa gccggctgtc gactgattgt gcttcacgtg     720
agcaaccctg acggggtcga gctgatacat caggcgcaat ccgagggcca ggacgtccac     780
tgcgagtcgg gtccgcagta tctgaatatc accacggacg acgccgaacg aatcggaccg     840
tatatgaagg tcgcgccgcc cgtccgctca gccgagatga acgtcagatt atgggaacaa     900
cttgagaacg ggctcatcga cacccttggg tcagaccacg gcggacatcc tgtcgaggac     960
aaagaacccg gctggaagga cgtgtggaaa gccggcaacg gtgcgctggg ccttgagaca    1020
tccctgccta tgatgctgac caacggagtg aataaaggca ggctatcctt ggaacgcctc    1080
gtcgaggtga tgtgcgagaa acctgcgaag ctctttggca tctatccgca gaagggcacg    1140
ctacaggttg gttccgacgc cgatctgctc atcctcgatc tggatattga caccaaagtg    1200
gatgcctcgc agttccgatc cctgcataag tacagcccgt tcgacgggat gcccgtcacg    1260
ggtgcaccgg ttctgacgat ggtgcgcgga acggtggtgg cagagaaggg agaagttctg    1320
gtcgagcagg gattcggcca gttcgtcacc cgtcacgact acgaggcgtc gaagtga       1377
```

<210> SEQ ID NO 10
<211> LENGTH: 458
<212> TYPE: PRT
<213> ORGANISM: Arthrobacter sp.

<400> SEQUENCE: 10

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Phe Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Ala Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190
```

-continued

Leu Gln Lys Gln Ile Lys Ala Ala Gly Arg Lys Asp Met Ala Ala Tyr
        195                 200                 205
Glu Ala Ser Gln Pro Val Phe Gln Glu Asn Glu Ala Ile Gln Arg Ala
    210                 215                 220
Leu Leu Leu Gln Lys Glu Ala Gly Cys Arg Leu Ile Val Leu His Val
225                 230                 235                 240
Ser Asn Pro Asp Gly Val Glu Leu Ile His Gln Ala Gln Ser Glu Gly
                245                 250                 255
Gln Asp Val His Cys Glu Ser Gly Pro Gln Tyr Leu Asn Ile Thr Thr
            260                 265                 270
Asp Asp Ala Glu Arg Ile Gly Pro Tyr Met Lys Val Ala Pro Pro Val
        275                 280                 285
Arg Ser Ala Glu Met Asn Val Arg Leu Trp Glu Gln Leu Glu Asn Gly
    290                 295                 300
Leu Ile Asp Thr Leu Gly Ser Asp His Gly His Pro Val Glu Asp
305                 310                 315                 320
Lys Glu Pro Gly Trp Lys Asp Val Trp Lys Ala Gly Asn Gly Ala Leu
                325                 330                 335
Gly Leu Glu Thr Ser Leu Pro Met Met Leu Thr Asn Gly Val Asn Lys
            340                 345                 350
Gly Arg Leu Ser Leu Glu Arg Leu Val Glu Val Met Cys Glu Lys Pro
        355                 360                 365
Ala Lys Leu Phe Glu Ile Tyr Pro Gln Lys Gly Thr Leu Gln Val Gly
    370                 375                 380
Ser Asp Ala Asp Leu Leu Ile Leu Asp Leu Asp Ile Asp Thr Lys Val
385                 390                 395                 400
Asp Ala Ser Gln Phe Arg Ser Leu His Lys Tyr Ser Pro Phe Asp Gly
                405                 410                 415
Met Pro Val Thr Gly Ala Pro Val Leu Thr Met Val Arg Gly Thr Val
            420                 425                 430
Val Ala Glu Lys Gly Glu Val Leu Val Glu Gln Gly Phe Gly Gln Phe
        435                 440                 445
Val Thr Arg His Asp Tyr Glu Ala Ser Lys
    450                 455

<210> SEQ ID NO 11
<211> LENGTH: 1377
<212> TYPE: DNA
<213> ORGANISM: Arthrobacter sp.

<400> SEQUENCE: 11
atgtttgacg taatagttaa gaactgccgt atggtgtcca gcgacggaat caccgaggca      60
gacattctgg tgaaagacgg caaagtcgcc gcaatcagct cggacacaag tgatgttgag     120
gcgagccgaa ccattgacgc gggtggcaag ttcgtgatgc cgggcgtggt cgatgaacat     180
gcgagccgaa ccattgacgc gggtggcaag ttcgtgatgc cgggcgtggt cgatgaacat     240
tctgcggccg tggaggcat caccaccatc atcgagatgc cgttaacctt cccgccccac     300
accactttgg acgccttcct gaaaagaag aagcaggcgg gcagcggtt gaaagttgac     360 ttcgcgctct atggcggtgg agtgccggga aacctgcccg agatccgcaa atgcacgac     420 gccggcgcag tgggcttcaa gtcaatgatg gcagcctcag ttccgggcat gttcgacgcc     480
gtcagcgacg gcgaactgtt cgaaatcttc caggagatcg cagcctgtgg ttcagtcgtc     540
gtggtccatg ccgagaatga aacgatcatt caagcgctcc agaagcagat caaagccgct     600

-continued

```
ggtcgcaagg acatggccgc ctacgaggca tcccaaccag ttttccagga gaacgaggcc    660
attcagcgtg cgttactact gcagaaagaa gccggctgtc gactgattgt gcttcacgtg    720
agcaaccctg acggggtcga gctgatacat caggcgcaat ccgagggcca ggacgtccac    780
tgcgagtcgg gtccgcagta tctgaatatc accacggacg acgccgaacg aatcggaccg    840
tatatgaagg tcgcgccgcc cgtccgctca gccgagatga acgtcagatt atgggaacaa    900
cttgagaacg ggctcatcga cacccttggg tcagaccacg gcggacatcc tgtcgaggac    960
aaagaacccg gctggaagga cgtgtggaaa gccggcaacg gtgcgctggg ccttgagaca   1020
tccctgccta tgatgctgac caacggagtg aataaaggca ggctatcctt ggaacgcctc   1080
gtcgaggtga tgtgcgagaa acctgcgaag ctctttggca tctatccgca gaagggcacg   1140
ctacaggttg gttccgacgc cgatctgctc atcctcgatc tggatattga caccaaagtg   1200
gatgcctcgc agttccgatc cctgcataag tacagcccgt tcgacgggat gcccgtcacg   1260
ggtgcaccgg ttctgacgat ggtgcgcgga acggtggtgg cagagaaggg agaagttctg   1320
gtcgagcagg gattcggcca gttcgtcacc cgtcacgact acgaggcgtc gaagtga      1377
```

<210> SEQ ID NO 12
<211> LENGTH: 458
<212> TYPE: PRT
<213> ORGANISM: Arthrobacter sp.

<400> SEQUENCE: 12

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Phe Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Leu Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240
```

```
Ser Asn Pro Asp Gly Val Glu Leu Ile His Arg Ala Gln Ser Glu Gly
            245                 250                 255
Gln Asp Val His Cys Glu Ser Gly Pro Gln Tyr Leu Asn Ile Thr Thr
        260                 265                 270
Asp Asp Ala Glu Arg Ile Gly Pro Tyr Met Lys Val Ala Pro Pro Val
        275                 280                 285
Arg Ser Ala Glu Met Asn Val Arg Leu Trp Glu Gln Leu Glu Asn Gly
        290                 295                 300
Leu Ile Asp Thr Leu Gly Ser Asp His Gly His Pro Val Glu Asp
305             310                 315                 320
Lys Glu Pro Gly Trp Lys Asp Val Trp Lys Ala Gly Asn Gly Ala Leu
                325                 330                 335
Gly Leu Glu Thr Ser Leu Pro Met Met Leu Thr Asn Gly Val Asn Lys
            340                 345                 350
Gly Arg Leu Ser Leu Glu Arg Leu Val Glu Val Met Cys Glu Lys Pro
            355                 360                 365
Ala Lys Leu Phe Glu Ile Tyr Pro Gln Lys Gly Thr Leu Gln Val Gly
        370                 375                 380
Ser Asp Ala Asp Leu Leu Ile Leu Asp Leu Asp Ile Asp Thr Lys Val
385             390                 395                 400
Asp Ala Ser Gln Phe Arg Ser Leu His Lys Tyr Ser Pro Phe Asp Gly
                405                 410                 415
Met Pro Val Thr Gly Ala Pro Val Leu Thr Met Val Arg Gly Thr Val
            420                 425                 430
Val Ala Glu Lys Gly Glu Val Leu Val Glu Gln Gly Phe Gly Gln Phe
        435                 440                 445
Val Thr Arg His Asp Tyr Glu Ala Ser Lys
        450                 455

<210> SEQ ID NO 13
<211> LENGTH: 1377
<212> TYPE: DNA
<213> ORGANISM: Arthrobacter sp.

<400> SEQUENCE: 13
atgtttgacg taatagttaa gaactgccgt atggtgtcca gcgacggaat caccgaggca      60
gacattctgg tgaaagacgg caaagtcgcc gcaatcagct cggacacaag tgatgttgag     120
gcgagccgaa ccattgacgc gggtggcaag ttcgtgatgc cgggcgtggt cgatgaacat     180
gcgagccgaa ccattgacgc gggtggcaag ttcgtgatgc cgggcgtggt cgatgaacat     240
tctgcggccg tgggaggcat caccaccatc atcgagatgc cgataacctt cccgcccacc     300
accactttgg acgccttcct gaaaagaag aagcaggcgg ggcagcggtt gaaagttgac     360
ttcgcgctct atggcggtgg agtgccggga aacctgcccg agatccgcaa atgcacgac      420
gccggcgcag tgggcttcaa gtcaatgatg gcagcctcag ttccgggcat gttcgacgcc     480
gtcagcgacg cgaactgtt cgaaatcttc caggagatcg cagcctgtgg ttcagtcgtc     540
gtggtccatg ccgagaatga aacgatcatt caagcgctcc agaagcagat caaagccgct     600
ggtcgcaagg acatggccgc ctacgaggca tcccaaccag ttttccagga gaacgaggcc     660
attcagcgtg cgttactact gcagaaagaa gccggctgtc gactgattgt gcttcacgtg     720
agcaaccctg acgggtcga gctgatacat caggcgcaat ccgagggcca ggacgtccac     780
tgcgagtcgg gtccgcagta tctgaatatc accacggacg acgccgaacg aatcggaccg     840
```

-continued

```
tatatgaagg tcgcgccgcc cgtccgctca gccgagatga acgccagatt atgggaacaa    900
cttgagaacg ggctcatcga caccettggg tcagaccacg gcggacatcc tgtcgaggac    960
aaagaacccg gctggaagga cgtgtggaaa gccggcaacg gtgcgctggg ccttgagaca   1020
tccctgccta tgatgctgac caacggagtg aataaaggca ggctatcctt ggaacgcctc   1080
gtcgaggtga tgtgcgagaa acctgcgaag ctctttggca tctatccgca gaagggcacg   1140
ctacaggttg gttccgacgc cgatctgctc atcctcgatc tggatattga caccaaagtg   1200
gatgcctcgc agttccgatc cctgcataag tacagcccgt tcgacgggat gcccgtcacg   1260
ggtgcaccgg ttctgacgat ggtgcgcgga acggtggtgg cagagaaggg agaagttctg   1320
gtcgagcagg gattcggcca gttcgtcacc cgtcacgact acgaggcgtc gaagtga      1377
```

<210> SEQ ID NO 14
<211> LENGTH: 458
<212> TYPE: PRT
<213> ORGANISM: Arthrobacter sp.

<400> SEQUENCE: 14

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Phe Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285
```

-continued

```
Arg Ser Ala Glu Met Asn Ala Arg Leu Trp Glu Gln Leu Glu Asn Gly
        290                 295                 300
Leu Ile Asp Thr Leu Gly Ser Asp His Gly Gly His Pro Val Glu Asp
305                 310                 315                 320
Lys Glu Pro Gly Trp Lys Asp Val Trp Lys Ala Gly Asn Gly Ala Leu
                325                 330                 335
Gly Leu Glu Thr Ser Leu Pro Met Met Leu Thr Asn Gly Val Asn Lys
            340                 345                 350
Gly Arg Leu Ser Leu Glu Arg Leu Val Glu Val Met Cys Glu Lys Pro
        355                 360                 365
Ala Lys Leu Phe Glu Ile Tyr Pro Gln Lys Gly Thr Leu Gln Val Gly
370                 375                 380
Ser Asp Ala Asp Leu Leu Ile Leu Asp Leu Asp Ile Asp Thr Lys Val
385                 390                 395                 400
Asp Ala Ser Gln Phe Arg Ser Leu His Lys Tyr Ser Pro Phe Asp Gly
                405                 410                 415
Met Pro Val Thr Gly Ala Pro Val Leu Thr Met Val Arg Gly Thr Val
            420                 425                 430
Val Ala Glu Lys Gly Glu Val Leu Val Glu Gln Gly Phe Gly Gln Phe
        435                 440                 445
Val Thr Arg His Asp Tyr Glu Ala Ser Lys
    450                 455
```

<210> SEQ ID NO 15
<211> LENGTH: 1377
<212> TYPE: DNA
<213> ORGANISM: Arthrobacter sp.

<400> SEQUENCE: 15

```
atgtttgacg taatagttaa gaactgccgt atggtgtcca gcgacggaat caccgaggca    60
gacattctgg tgaaagacgg caaagtcgcc gcaatcagct cggacacaag tgatgttgag   120
gcgagccgaa ccattgacgc gggtggcaag ttcgtgatgc cgggcgtggt cgatgaacat   180
gcgagccgaa ccattgacgc gggtggcaag ttcgtgatgc cgggcgtggt cgatgaacat   240
tctgcggccg tgggaggcat caccaccatc atcgagatgc cgttaacctt cccgcccacc   300
accactttgg acgccttcct cgaaaagaag aagcaggcgg ggcagcggtt gaaagttgac   360
ttcgcgctct atggcggtgg agtgccggga aacctgcccg agatccgcaa aatgcacgac   420
gccggcgcag tgggcttcaa gtcaatgatg gcagcctcag ttccgggcat gttcgacgcc   480
gtcagcgacg gcgaactgtt cgaaatcttc caggagatcg cagcctgtgg ttcagtcgtc   540
gtggtccatg ccgagaatga aacgatcatt caagcgctcc agaagcagat caaagccgct   600
ggtcgcaagg acatggccgc ctacgaggca tcccaaccag ttttccagga gaacgaggcc   660
attcagcgtg cgttactact gcagaaagaa gccggctgtc gactgattgt gcttcacgtg   720
agcaaccctg acgggtcga gctgatacat caggcgcaat ccgagggcca ggacgtccac   780
tgcgagtcgg gtccgcagta tctgaatatc accacggacg acgccgaacg aatcggaccg   840
tatatgaagg tcgcgccgcc cgtccgctca gccgaaatga acgtcagatt atgggaacaa   900
cttgagaacg ggctcatcga caccctgggg tcagaccacg gcgacatcc tgtcgaggac   960
aaagaacccg gctggaagga cgtgtggaaa gccggcaacg gtgcgctggg ccttgagaca  1020
tccctgccta tgatgctgac caacggagtg aataaaggca ggctatcctt ggaacgcctc  1080
gtcgaggtga tgtgcgagaa acctgcgaag ctctttggca tctatccgca agagggcacg  1140
```

```
ctacaggttg gttccgacgc cgatctgctc atcctcgatc tggatattga caccaaagtg    1200
gatgcctcgc agttccgatc cctgcataag tacagcccgt tcgacgggat gcccgtcacg    1260
ggtgcaccgg ttctgacgat ggtgcgcgga acggtggtgg cagagaaggg agaagttctg    1320
gtcgagcagg gattcggcca gttcgtcacc cgtcacgact acgaggcgtc gaagtga       1377
```

<210> SEQ ID NO 16
<211> LENGTH: 458
<212> TYPE: PRT
<213> ORGANISM: Arthrobacter sp.

<400> SEQUENCE: 16

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Phe Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Leu Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335
```

```
Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Glu Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 17
<211> LENGTH: 1377
<212> TYPE: DNA
<213> ORGANISM: Arthrobacter sp.

<400> SEQUENCE: 17
atgtttgacg taatagttaa gaactgccgt atggtgtcca gcgacggaat caccgaggca     60
gacattctgg tgaaagacgg caaagtcgcc gcaatcagct cggacacaag tgatgttgag    120
gcgagccgaa ccattgacgc gggtggcaag ttcgtgatgc cgggcgtggt cgatgaacat    180
gcgagccgaa ccattgacgc gggtggcaag ttcgtgatgc cgggcgtggt cgatgaacat    240
tctgcggccg tgggaggcat caccaccatc atcgagatgc cgttaacctt cccgcccacc    300
accactttgg acgccttcct cgaaaagaag aagcaggcgg ggcagcggtt gaaagttgac    360
ttcgcgctct atggcggtgg agtgccggga aacctgcccg agatccgcaa aatgcacgac    420
gccggcgcag tgggcttcaa gtcaatgatg gcagcctcag ttccgggcat gttcgacgcc    480
gtcagcgacg gcgaactgtt cgaaatcttc caggagatcg cagcctgtgg ttcagtcgcc    540
gtggtccatg ccgagaatga acgatcatt caagcgctcc agaagcagat caaagccgct    600
ggtcgcaagg acatggccgc ctacgaggca tcccaaccag ttttccagga gaacgaggcc    660
attcagcgtg cgttactact gcagaaagaa gccggctgtc gactgattgt gcttcacgtg    720
agcaaccctg acggggtcga gctgatacat cgggcgcaat ccgagggcca ggacgtccac    780
tgcgagtcgg gtccgcagta tctgaatatc accacggacg acgccgaacg aatcggaccg    840
tatatgaagg tcgcgccgcc cgtccgctca gccgagatga acgtcagatt atgggaacaa    900
cttgagaacg ggctcatcga caccttggg tcagaccacg gcggacatcc tgtcgaggac    960
aaagaacccg gctggaagga cgtgtggaaa gccggcaacg gtgcgctggg ccttgagaca   1020
tccctgccta tgatgctgac caacggagtg aataaaggca ggctatcctt ggaacgcctc   1080
gtcgaggtga tgtgcgagaa acctgcgaag ctctttggca tctatccgca gaagggcacg   1140
ctacaggttg gttccgacgc cgatctgctc atcctcgatc tggatattga caccaaagtg   1200
gatgcctcgc agttccgatc cctgcataag tacagcccgt tcgacgggat gcccgtcacg   1260
ggtgcaccgg ttctgacgat ggtgcgcgga acggtggtgg cagagaaggg agaagttctg   1320
gtcgagcagg gattcggcca gttcgtcacc cgtcacgact acgaggcgtc gaagtga      1377
```

<210> SEQ ID NO 18
<211> LENGTH: 458
<212> TYPE: PRT
<213> ORGANISM: Arthrobacter sp.

<400> SEQUENCE: 18

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Phe Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Val Gly Gly Ile Thr Thr Ile Ile Glu Met Pro Leu Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Ala Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Arg Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Glu Ile Tyr Pro Gln Lys Gly Thr Leu Gln Val Gly
    370                 375                 380
```

```
Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
            405                 410                 415

Met Pro Val Thr Gly Ala Pro Val Leu Thr Met Val Arg Gly Thr Val
        420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455
```

<210> SEQ ID NO 19
<211> LENGTH: 1377
<212> TYPE: DNA
<213> ORGANISM: Arthrobacter sp.

<400> SEQUENCE: 19

```
atgtttgacg taatagttaa gaactgccgt atggtgtcca gcgacggaat caccgaggca      60
gacattctgg tgaaagacgg caaagtcgcc gcaatcagct cggacacaag tgatgttgag     120
gcgagccgaa ccattgacgc gggtggcaag ttcgtgatgc cgggcgtggt cgatgaacat     180
gcgagccgaa ccattgacgc gggtggcaag ttcgtgatgc cgggcgtggt cgatgaacat     240
tctgcggccg tgggaggcat caccaccatc atcgagatgc cgtttacctt cccgcccacc     300
accactttgg acgccttcct cgaaaagaag aagcaggcgg ggcagcggtt gaaagttgac     360
ttcgcgctct atggcggtgg agtgccggga acctgcccg agatccgcaa aatgcacgac     420
gccggcgcag tgggcttcaa gtcaatgatg gcagcctcag ttccgggcat gttcgacgcc     480
gtcagcgacg gcgaactgtt cgaaatcttc caggagatcg cagcctgtgg ttcagtcgcc     540
gtggtccatg ccgagaatga acgatcatt caagcgctcc agaagcagat caaagccgct     600
ggtcgcaagg acatggccgc ctacgaggca tcccaaccag ttttccagga gaacgaggcc     660
attcagcgtg cgttactact gcagaaagaa gccggctgtc gactgattgt gcttcacgtg     720
agcaaccctg acggggtcga gctgatacat cgggcgcaat ccgagggcca ggacgtccac     780
tgcgagtcgg gtccgcagta tctgaatatc accacggacg acgccgaacg aatcggaccg     840
tatatgaagg tcgcgccgcc cgtccgctca gccgagatga acgtcagatt atgggaacaa     900
cttgagaacg ggctcatcga caccttgggt caggaccacg gcggacatcc tgtcgaggac     960
aaagaacccg gctggaagga cgtgtggaaa gccggcaacg gtgcgctggg ccttgagaca    1020
tccctgccta tgatgctgac aacggagtg aataaaggca ggctatcctt ggaacgcctc    1080
gtcgaggtga tgtgcgagaa acctgcgaag ctctttggca tctatccgca gaagggcacg    1140
ctacaggttg gttccgacgc cgatctgctc atcctcgatc tggatattga caccaaagtg    1200
gatgcctcgc agttccgatc cctgcataag tacagcccgt tcgacgggat gcccgtcacg    1260
ggtgcaccgg ttctgacgat ggtgcgcgga acggtggtgg cagagaaggg agaagttctg    1320
gtcgagcagg gattcggcca gttcgtcacc cgtcacgact acgaggcgtc gaagtga       1377
```

<210> SEQ ID NO 20
<211> LENGTH: 458
<212> TYPE: PRT
<213> ORGANISM: Arthrobacter sp.

<400> SEQUENCE: 20

Met Phe Asp Val Ile Val Lys Asn Cys Arg Met Val Ser Ser Asp Gly

-continued

```
1               5                   10                  15
Ile Thr Glu Ala Asp Ile Leu Val Lys Asp Gly Lys Val Ala Ile
                20                  25                  30

Ser Ser Asp Thr Ser Asp Val Glu Ala Ser Arg Thr Ile Asp Ala Gly
        35                  40                  45

Gly Lys Phe Val Met Phe Gly Val Val Asp Glu His Val His Ile Ile
        50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Phe Thr
                85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
                115                 120                 125

Pro Gly Asn Leu Pro Glu Ile Arg Lys Met His Asp Ala Gly Ala Val
                130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Ala Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
                195                 200                 205

Glu Ala Ser Gln Pro Val Phe Gln Glu Asn Glu Ala Ile Gln Arg Ala
                210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Arg Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
                275                 280                 285

Arg Ser Ala Glu Met Asn Val Arg Leu Trp Glu Gln Leu Glu Asn Gly
                290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
                355                 360                 365

Ala Lys Leu Phe Glu Ile Tyr Pro Gln Lys Gly Thr Leu Gln Val Gly
                370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430
```

```
Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 21
<211> LENGTH: 30
<212> TYPE: DNA
<213> ORGANISM: Artificial Sequence
<220> FEATURE:
<223> OTHER INFORMATION: Synthetic DNA

<400> SEQUENCE: 21
agaacatatg tttgacgtaa tagttaagaa                                    30

<210> SEQ ID NO 22
<211> LENGTH: 28
<212> TYPE: DNA
<213> ORGANISM: Artificial Sequence
<220> FEATURE:
<223> OTHER INFORMATION: Synthetic DNA

<400> SEQUENCE: 22
aaaaggatcc tcacttcgac gcctcgta                                      28

<210> SEQ ID NO 23
<211> LENGTH: 30
<212> TYPE: DNA
<213> ORGANISM: Artificial Sequence
<220> FEATURE:
<223> OTHER INFORMATION: Synthetic DNA

<400> SEQUENCE: 23
aggcgacata tgaccctgca gaaagcgcaa                                    30

<210> SEQ ID NO 24
<211> LENGTH: 30
<212> TYPE: DNA
<213> ORGANISM: Artificial Sequence
<220> FEATURE:
<223> OTHER INFORMATION: Synthetic DNA

<400> SEQUENCE: 24
atgggatccc cggtcaagtg ccttcattac                                    30
```